United States Patent [19]
Wu

[11] Patent Number: 5,599,388
[45] Date of Patent: Feb. 4, 1997

[54] ACID RESISTANT CALCIUM CARBONATE COMPOSITION CONTAINING AN ALUMINUM SALT, USES THEREFOR AND PROCESSES FOR ITS PRODUCTION

[75] Inventor: Kuan-Ting Wu, Sandersville, Ga.

[73] Assignee: ECC International Inc., Atlanta, Ga.

[21] Appl. No.: 518,763

[22] Filed: Aug. 24, 1995

[51] Int. Cl.$^6$ .................................... C09C 1/02
[52] U.S. Cl. .................. 106/464; 162/181.2; 162/181.3; 162/183
[58] Field of Search .................... 106/464, 465; 162/181.2, 181.3, 183

[56] References Cited

U.S. PATENT DOCUMENTS

| | | | |
|---|---|---|---|
| 4,115,187 | 9/1978 | Davidson | 162/183 |
| 5,000,791 | 3/1991 | Tokarz et al. | 106/465 |
| 5,043,017 | 8/1991 | Passaretti et al. | 106/464 |
| 5,221,435 | 6/1993 | Smith, Jr. | 162/181.2 |

FOREIGN PATENT DOCUMENTS 0099547  2/1984  European Pat. Off. .

OTHER PUBLICATIONS

Rodriguez, J. M. (1991) Papermkers Conference 91:5–8. (no month).

Primary Examiner—Mark L. Bell
Assistant Examiner—Michael Marcheschi
Attorney, Agent, or Firm—Klauber & Jackson

[57] ABSTRACT

An improved form of calcium carbonate which is acid resistant to enable its use as a filler material in the making of neutral to weakly acid paper, and a process for producing this acid resistant calcium carbonate are provided. This acid resistant calcium carbonate comprises a mixture of at least about 0.5 to about 10 percent of an aluminum salt, based on the dry weight of calcium carbonate, and calcium carbonate. Preferred aluminum salts are aluminum sulfate, aluminum chloride, and polyaluminum chloride.

17 Claims, 4 Drawing Sheets

ACID RESISTANT CALCIUM CARBONATE COMPOSITION CONTAINING AN ALUMINUM SALT, USES THEREFOR AND PROCESSES FOR ITS PRODUCTION

BACKGROUND OF THE INVENTION

This invention relates generally to calcium carbonate for use in papermaking, and related industries, and more particularly to a calcium carbonate having acid resistant properties.

Titanium dioxide mid calcined clay have traditionally been utilized as filler materials in the preparation of neutral to weakly acidic paper in order to improve the optical properties, especially the brightness, of the resultant product. These materials, however, especially titanium dioxide, have the disadvantage of being very expensive, resulting in higher manufacturing costs and an uncompetitively priced paper product.

Calcium carbonate, particularly precipitated calcium carbonate, has been used as a filler material in the making of alkaline paper. Such usage results in a paper with enhanced optical properties, without the expense incurred in using titanium oxide fillers, resulting in a much less expensive product. Calcium carbonate, however, cannot generally be used as a filler in acidic paper because it decomposes in an acidic environment. Consequently, there has long been a need to develop a calcium carbonate composition which is acid stabilized and resistant to decomposition at low pH, so that it can be utilized as a filler material in the manufacture of acidic paper, such as groundwood paper, where the use of an alkaline filler would have a negative impact on the final paper properties.

A particular disadvantage of calcium carbonate, when used as a filler in paper, is its reaction with alum which is also commonly used in papermaking. Alum (aluminum sulfate $[Al_2(SO_4)_3 18H_2O]$), produces aluminum hydroxide and sulfuric acid when added to the "wet" papermaking system. The flocculation of aluminum hydroxide is capable of collecting and retaining the filler and also part of the resin-alum system for paper sizing. During manufacture, the alum flocks in the paper web are removed, and the sulfuric acid is increasingly concentrated in the white water, in spite of the buffer action of the system. The presence of calcium carbonate in a system of pH 4 will quickly consume part of the sulfuric acid, thereby forming calcium sulfate and free $Ca^{++}$ ions. The presence of these ions in the recycled white water causes a considerable reduction of the sizing effect in the papermaking pulp, and this, in turn, necessitates the use of large amounts of alum to maintain stable sizing conditions.

In the manufacture of paper, dewatering and retention were improved by adding to the stock a water-soluble aluminum chloride, aluminum hydroxychloride, viz. $Al_2(OH)_5Cl$, or polyaluminum chloride, $[Al_2(OH)_nCl_{6-n}]_m$. Polyaluminum chloride varies substantially according to the manufacturing procedure, and the process kinetics of degree of neutralization affect both the product produced and its reactions in the papermaking system. In neutral and alkaline papermaking systems, polyaluminum chlorides (from simple to highly complex polymers) can be used for pitch control, drainage, retention, and sizing. On the other hand, the surface charge and zeta potential of aluminum chloride are higher than those of alum from 3.5 to 8 pH range.

A variety of techniques to modify calcium carbonate to achieve acid resistance and avoid the aforementioned problems are disclosed in the art. For instance, U.S. Pat. No. 5,043,017 discloses and claims an acid-stable calcium carbonate resistant to degradation in a mildly acidic environment which comprises a mixture of a calcium-chelating agent or a conjugate base, and a weak acid such that calcium carbonate is coated by and is in equilibrium with the calcium-chelating agent or conjugate base and the weak acid. Preferred calcium carbonate compositions contain sodium hexametaphosphate and phosphoric acid. U.S. Pat. No. 5,000,791 discloses an acid-resistant coating on calcium carbonate particles consisting of a zinc compound and a solution of a silica-containing substance.

OBJECTS OF THE INVENTION

It is an object of the present invention to provide an acid resistant calcium carbonate composition especially suitable for use in papermaking applications.

It is a further object of the present invention to provide a process for the preparation of the aforesaid calcium carbonate compositions.

A still further object of the present invention is to provide a paper having enhanced optical qualities prepared using the calcium carbonate compositions of the present invention.

SUMMARY OF THE INVENTION

The present invention relates to an improved form of calcium carbonate which is acid resistant to enable its use as a filler material in the making of neutral to weakly acid paper, and a process for producing this acid resistant calcium carbonate. More particularly, this invention concerns an acid resistant calcium carbonate comprising a mixture of at least about 0.5 to about 10 percent, based on the dry weight of the calcium carbonate, of an aluminum salt in admixture with the calcium carbonate.

DETAILED DESCRIPTION OF THE INVENTION

The improved form of calcium carbonate prepared by the instant invention is acid resistant to enable its use as a filler material in the making of neutral to weakly acid paper. While not wishing to be bound by any particular theory as to the operability of the present invention, it is believed that the acid resistance conferred upon the calcium carbonate compositions of the present invention is a result of the inactivation of the surface of the calcium carbonate by the addition of the aluminum salt.

In the practice of the present invention, the calcium carbonate compositions are rendered acid resistant by the inclusion of at least about 0.5 to about 10 percent, based on the dry weight of the calcium carbonate, of an aluminum salt in the calcium carbonate composition. Preferably, the aluminum salt is included in the composition in an amount of about 2 to about 5 percent, based on the dry weight of the calcium carbonate. The calcium carbonate utilized is preferably finely divided and it can be either a precipitated calcium carbonate or a natural ground limestone.

Aluminum salts utilizable in the present invention include aluminum sulfate, aluminum ammonium sulfate, aluminum potassium sulfate, chromium ammonium sulfate, aluminum hydroxychloride, $Al_2(OH)_5Cl$, polyaluminum chloride, $[Al_2(OH)_nCl_{6-n}]_m$ and aluminum chloride, as well as hydrates and mixtures thereof.

The process for producing this acid resistant calcium carbonate involves forming a mixture of calcium carbonate with at least about 0.5 to about 10 percent, based on the dry weight of calcium carbonate, aluminum salt, and blending the resultant mixture for a sufficiently long period of time to ensure uniform mixing of the ingredients.

The calcium carbonate can be utilized in the above-described process either as a dry powder or an aqueous slurry with up to about 70 percent by weight solids content.

The aluminum salt can be utilized in the instant process either as a dry solid or and an aqueous solution. When the calcium carbonate is used in dry powder form, it is necessary to utilize an aqueous solution of the aluminum salt in order to facilitate homogeneous mixing. Where a slurry of the calcium carbonate is utilized, the solid form of the aluminum salt readily dissolves therein so that an aqueous solution is unnecessary.

The composition of the present invention can be utilized to improve the optical properties of neutral to weakly acidic paper by its addition to the paper during standard manufacturing processes. Typically, the calcium carbonate composition of the present invention is added to a first paper furnish containing components necessary for making acidic paper to thereby form a second paper furnish.

The invention will be further illustrated by the following Examples, which are to be considered illustrative of the invention, and not limited to the precise embodiments shown.

EXAMPLE 1

Scalenohedral Precipitated Calcium Carbonate Composition

Figure 1:
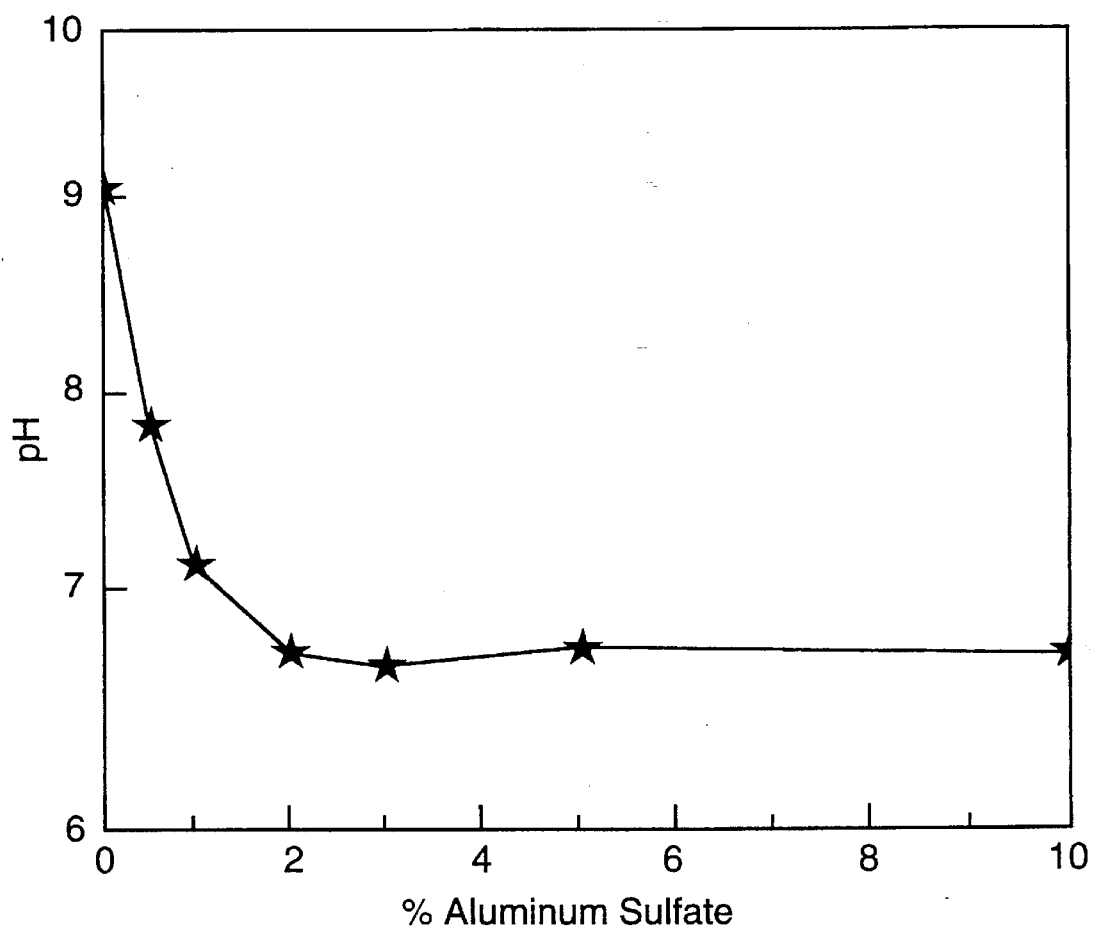
FIG. 1 is a graph showing the pH at 24 hours ageing of scalenohedral precipitated calcium carbonate compositions of the present invention using various concentrations of aluminum sulfate.

Acid resistant calcium carbonate slurry can be obtained by the addition of aluminum sulfate. The pH of scalenohedral precipitated calcium carbonate slurry was 9.05, with a solids content of 19.7% Initially, 0.5,1, 2, 3, 5, and 10% aluminum sulfate, based on the dry weight of calcium carbonate, was added into the slurry of scalenohedral precipitated calcium carbonate. The pH was read after 5 minutes of mixing. The pH was again measured for each sample after 24 hours ageing, and the graph of the pH plotted versus % alum is shown in FIG. 1. As indicated in FIG. 1, the initial pH of a calcium carbonate composition containing 2% aluminum sulfate, based on the dry weight of calcium carbonate, was 6.71. After 24 hours ageing, the pH was 6.75.

EXAMPLE 2

Ground Calcium Carbonate Composition

Figure 2:
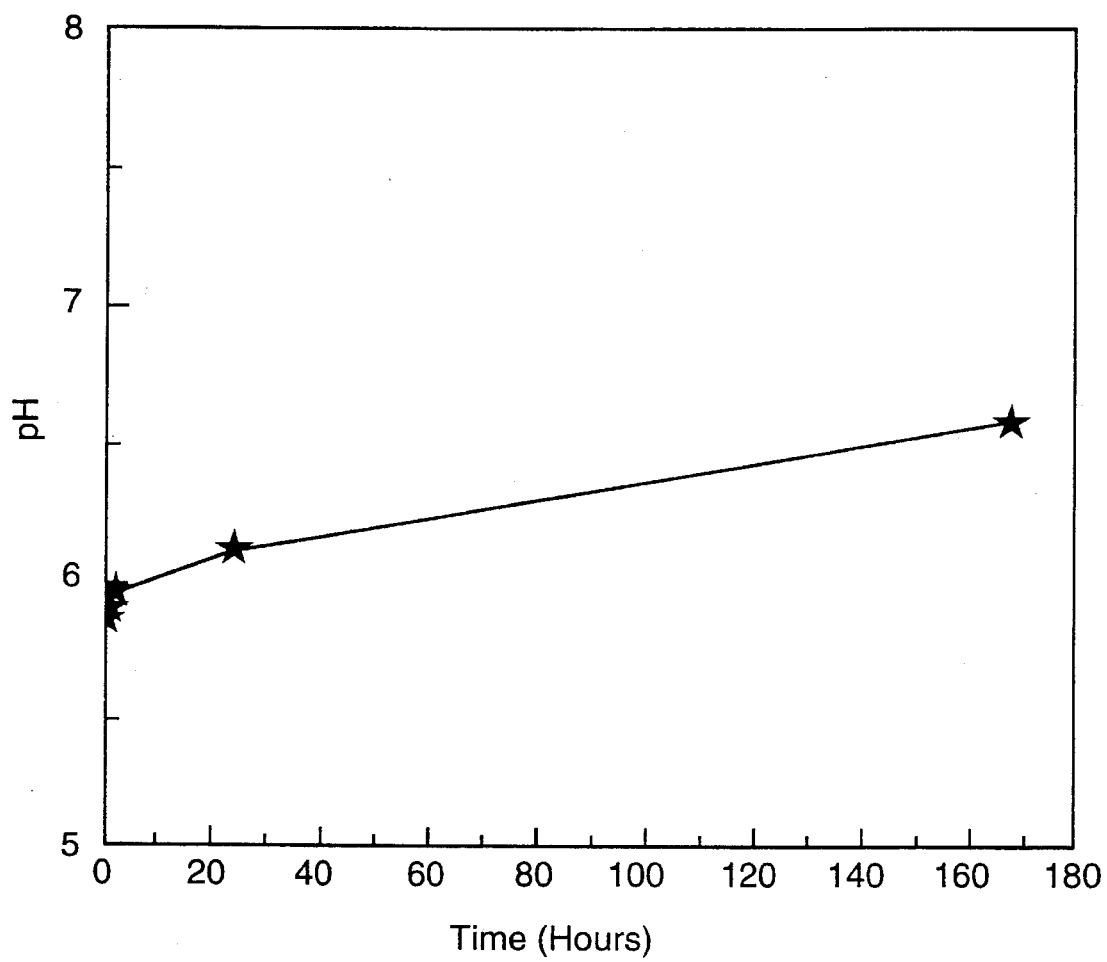
FIG. 2 is a graph showing the pH versus time of a ground calcium carbonate/4% aluminum sulfate composition.

The initial pH of ground calcium carbonate slurry was 8.01. Four percent aluminum sulfate, based on the dry weight of calcium carbonate, was added into the slurry. After blending for five minutes, the pH was measured and found to be 5.89. After seven days ageing, it was again measured and found to be 6.59, as shown in FIG. 2. The final solids content of the ground calcium carbonate slurry was 20.0%.

EXAMPLE 3

Comparison of Calcium Carbonate Compositions in Paper Making Process

As in the papermaking process, 5.08 grams precipitated calcium carbonate (19.7% solids) was added into 400 mL fiber slurry (0.3% solids, pH=6.52). After mixing for 5 minutes, the pH was measured and found to be 8.16.

This process was then repeated using 5.3 grams of a precipitated calcium carbonate/2% aluminum sulfate composition (prepared according to the procedure of Example 1, 19.0% solids), and 400 mL fiber slurry (0.3% solids, pH=6.52). After blending for 5 minutes, the pH was measured and found to be 7.84.

EXAMPLE 4

Rhombic Precipitated Calcium Carbonate Composition

Figure 3:
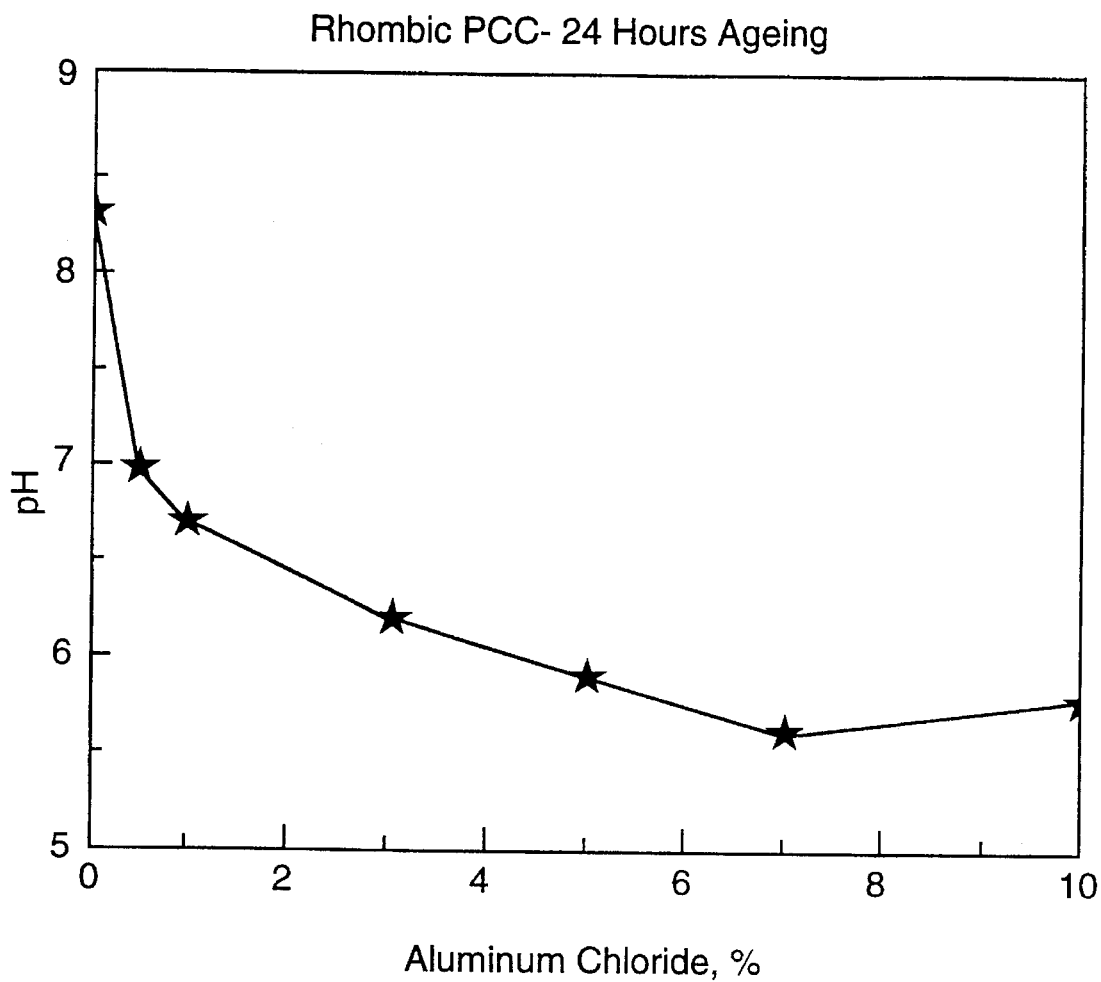
FIG. 3 is a graph showing the pH at 24 hours ageing of rhombic precipitated calcium carbonate compositions of the present invention using various concentrations of aluminum chloride.

Acid stabilized ground calcium carbonate slurry was prepared by aluminum chloride treatment. The initial pH of rhombic precipitated calcium carbonate slurry was 8.29, and the solids content was 17.3%. To this was added 0.5, 1, 3, 5, 7 and 10% aluminum chloride, based on the dry weight of calcium carbonate, with mixing. The pH was read after mixing 5 minutes. A plot of pH was measured for each sample after 24 hours ageing as shown in FIG. 3. For a rhombic precipitated calcium carbonate composition containing 5% aluminum chloride, based on the dry weight of calcium carbonate; the initial pH of the slurry was 5.86. After 24 hours ageing the pH was 5.92

EXAMPLE 5

Scalenohedral Precipitated Calcium Carbonate Composition

Figure 4:
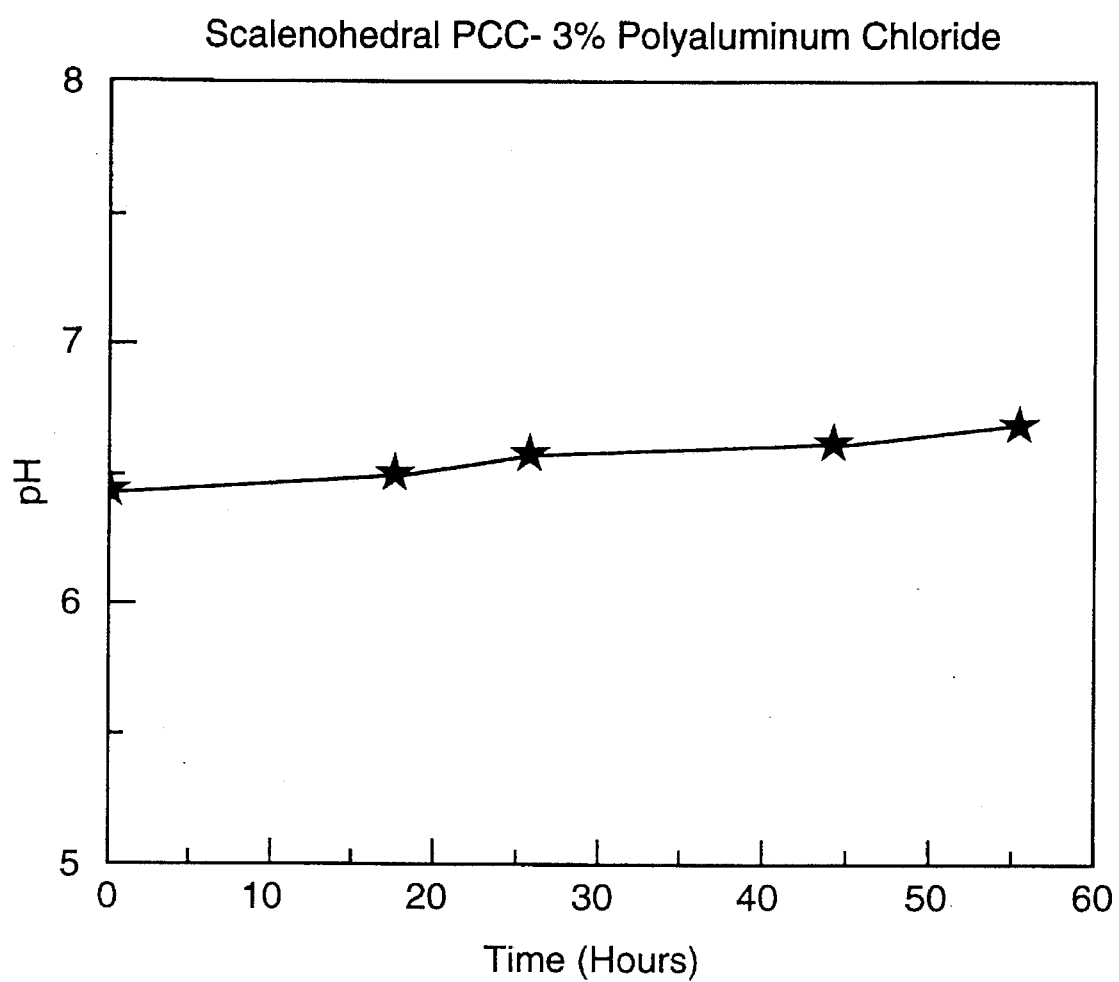
FIG. 4 is a graph showing the pH versus time of a scalenohedral precipitated calcium carbonate/3% polyaluminum chloride composition.

Acid stabilized scalenohedral precipitated calcium carbonate was made by polyaluminum chloride treatment. The initial pH of scalenohedral precipitated calcium carbonate slurry was 9.05, and the solids content was 19.7%. To this was added 3% polyaluminum chloride, based on the dry weight of calcium carbonate, with mixing. The pH was read after mixing 5 minutes. A plot of pH was measured after 55 hours aging as shown in FIG. 4. The initial pH of the acid stabilized scalenohedral precipitated calcium carbonate slurry was 6.45. The final pH of the slurry was found to be 6.71 after 55 hours aging.

What is claimed is:

1. An acid resistant calcium carbonate composition wherein the composition is made acid resistant by an ingredient consisting essentially of; at least 0.5 to about 10 percent aluminum salt, based on the dry weight of the calcium carbonate.

2. The acid resistant calcium carbonate of claim 1 wherein the aluminum salt is present in an amount of about 2 to about 5 percent, based on the dry weight of the calcium carbonate.

3. The acid resistant calcium carbonate of claim 1 wherein the aluminum salt is aluminum sulfate.

4. The acid resistant calcium carbonate of claim 1 wherein the aluminum salt is aluminum chloride.

5. The acid resistant calcium carbonate of claim 1 wherein the aluminum salt is polyaluminum chloride.

6. A process for the preparation of an acid resistant calcium carbonate composition which comprises:
   a) forming a mixture of calcium carbonate with at least about 0.5 to about 10 percent aluminum salt, based on the dry weight of the calcium carbonate; and
   b) blending said mixture to ensure uniform mixing.

7. The process according to claim 6 wherein the aluminum salt is present in an amount of about 2 to about 5 percent, based on the dry weight of the calcium carbonate.

8. The process according to claim 6 wherein the aluminum salt is aluminum sulfate.

9. The process according to claim 6 wherein the aluminum salt is aluminum chloride.

10. The process according to claim 6 wherein the aluminum salt is polyaluminum chloride.

11. The process according to claim 6 wherein the calcium carbonate is utilized as a slurry.

12. The process according to claim 6 wherein the aluminum salt is used as an aqueous solution.

13. A method of improving optical properties of neutral to weakly acidic paper which comprises adding to said paper an acid resistant calcium carbonate composition, wherein the composition is made acid resistant by an ingredient consisting essentially of at least 0.5 to about 10 percent aluminum salt, based on the dry weight of the calcium carbonate.

14. The method according to claim 13 wherein the aluminum salt is present in the calcium carbonate composition in an amount of about 2 to about 5 percent, based on the dry weight of the calcium carbonate.

15. The method according to claim 13 wherein the aluminum salt is aluminum sulfate.

16. The method according to claim 13 wherein the aluminum salt is aluminum chloride.

17. The method according to claim 13 wherein the aluminum salt is polyaluminum chloride.

* * * * *